US008865910B2

(12) United States Patent
Sarkar et al.

(10) Patent No.: US 8,865,910 B2
(45) Date of Patent: Oct. 21, 2014

(54) 1, 2, 4-TRIAZOLE DERIVATIVES AND THEIR ANTI MYCOBACTERIAL ACTIVITY

(75) Inventors: Dhiman Sarkar, Pune (IN); Sunita Ranjan Deshpande, Pune (IN); Shailaja Pramod Maybhate, Pune (IN); Anjali Prabhakar Likhite, Pune (IN); Sampa Sarkar, Pune (IN); Arshad Khan, Pune (IN); Preeti Madhukar Chaudhary, Pune (IN); Sayalee Ramchandra Chavan, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/634,352

(22) PCT Filed: Mar. 14, 2011

(86) PCT No.: PCT/IN2011/000172

§ 371 (c)(1),
(2), (4) Date: Nov. 16, 2012

(87) PCT Pub. No.: WO2011/111077

PCT Pub. Date: Sep. 15, 2011

(65) Prior Publication Data

US 2013/0060045 A1 Mar. 7, 2013

(30) Foreign Application Priority Data

Mar. 12, 2010 (IN) .......................... 0574/DEL/2010

(51) Int. Cl.
*A61K 31/41* (2006.01)
*C07D 403/00* (2006.01)
*C07D 249/06* (2006.01)

(52) U.S. Cl.
CPC .................................. *C07D 249/06* (2013.01)
USPC .......................................... 548/255; 514/383

(58) Field of Classification Search
CPC .................................................... C07D 249/06
See application file for complete search history.

(56) References Cited

U.S. PATENT DOCUMENTS 8,119,693 B2 * 2/2012 Millan et al. .................. 514/604
2006/0247280 A1 * 11/2006 Marino et al. ................ 514/341
2009/0156560 A1 6/2009 Millan et al.

FOREIGN PATENT DOCUMENTS

CH 484 920 1/1970
GB 1508757 A 4/1978

OTHER PUBLICATIONS

CAPLUS 1986:514990.*
CAPLUS 1995:965994.*

Preeti M. Chaudhary, et al; "Structural elucidation of propargylated products of 3-substituted-1,2,4-triazole-5-thiols by NMR techniques", Magn. Reson. Chem. vol. 146, pp. 1168-1174, Published Online Oct. 13, 2008.

Alireza Foroumadi, et al; "Antituberculosis Agents X. Synthesis and Evaluation of In Vitro Antituberculosis Activity of 2-(5-Nitro-2-furyl)- and 2-(1-Methyl-5-nitro-1*H*-imidazol-2-yl)-1,3,4-thiadiazole Derivatives", Arch. Pharm. Res. vol. 27, No. 5, pp. 502-506; May 2004.

Majid. M. Heravi, et al; "Sodium Hydroxide: a Mild and Inexpensive Catalyst for the Regioselective Synthesis of 2-Substituted 5-Methylthiazolo[3,2-*b*]-s-triazoles", J. Chem. Research (Synopses), pp. 488-489, 1998 exact date not given online.

B. Shivarma Holla, et al; "Synthesis and biological activity of some bistriazole derivatives", Indian Journal of Chemistry, vol. 42B, Aug. 2003, pp. 2010-2014.

(Continued)

*Primary Examiner* — Heidi Reese
(74) *Attorney, Agent, or Firm* — Ladas & Parry LLP

(57) ABSTRACT

Invention provides antitubercular compounds selected from propargylated 1,2,3 triazoles of Formula I, wherein, X is sulfur(S) or a sulphone (A), n, m represent independently an integer O or 1, with the provision that when 'n' is 1, 'm' is 1; R1 is hydrogen; C1-C6 linear or branched alkyl group optionally substituted with aryl group; halogen; or aryl group optionally substituted with —OCH3, halogen, and nitro; R2 and R3 are selected from the group consisting of hydrogen, C1-C6 alkyl optionally substituted with heterocyclic ring of 5 to 6 ring atoms containing one to three hetero atoms selected from oxygen, sulfur, nitrogen, which may be substituted with alkyl, arylalkyl, linear or branched alkenyl, substituted alkenyl, alkynyl, substituted alkynyl, or allyl or propargyl groups consisting of 1 to 6 carbon atoms; Z is C1-C6 alkyl optionally substituted with heterocyclic ring of 1 to 6 ring atoms, containing one to three hetero atoms selected from oxygen, sulfur, nitrogen, which may be substituted with arylalkyl, linear or branched alkenyl, substituted alkenyl, alkynyl, substituted alkynyl allyl or propargyl groups consisting of 1 to 6 carbon atoms; with the provision that when 'm' is 1, and 'n' is zero; R1 is selected from the group consisting of hydrogen, halogen; C1-C6 linear or branched alkyl group optionally substituted with aryl group or aryl group optionally substituted with —OCH3, halogen, and nitro, R2 and R3 are selected from the group consisting of hydrogen, C1-C6 alkyl optionally substituted with heterocyclic ring of 5 to 6 ring atoms containing one to three hetero atoms selected from oxygen, sulfur, nitrogen, which may be substituted with alkyl, arylalkyl, linear or branched alkenyl, substituted alkenyl, alkynyl, substituted alkynyl, or allyl or propargyl groups consisting of 1 to 6 carbon atoms; Z is selected from the group consisting of halogen, C1-C6 linear or branched alkyl group optionally substituted with heterocyclic ring of 1 to 6 ring atoms, containing one to three hetero atoms selected from oxygen, sulfur, nitrogen, wherein the heterocyclic ring may further be substituted with halogen, alkyl, arylalkyl.

3 Claims, 2 Drawing Sheets

(56) References Cited

OTHER PUBLICATIONS

Ilkay Kucukguzel, et al "Synthesis of some novel thiourea derivatives obtained from 5-[(4-aminophenoxy)methyl]-4-alkyl/aryl-2,4-dihydro-3*H*-1,2,4-triazole-3-thiones and evaluation as antiviral/anti-HIV and anti-tuberculosis agents", European Jounral of Medicinal Chemistry, vol. 43, pp. 381-392, Available online May 13, 2007.

Ajay Kumar, et al; "Synthesis of novel heterocyclic compounds: Routes to pyrazolyl 1,2,3-triazoles and biological activity evaluation", Indian Journal of Chemistry, vol. 42B, Aug. 2003, pp. 1950-1957.

Ahmed Ozdemir, et al; "Synthesis of some 4-arylidenamino-4H-1,2,4-triazole-3-thiols and their antituberculosis activity", Journal of Enzyme Inhibition and Medicinal Chemistry, Aug. 2007, vol. 22, No. 4, pp. 511-516.

Mahendra Shiradkar, et al; "Microwave assisted synthesis and antimicrobial screening of fused triazoles", Arkivoc, pp. 141-154, Jan. 2006.

L.G. Tikhonova, et al; "Synthesis of Noncondensed Polynuclear Vicinal Triazoles", Chemistry of Heterocyclic Compounds Dec. 1981, vol. 17, Issue 12, pp. 1241-1244.

Isaac M. Westwood, et al; "Identification of arylamine *N*-acetyltransferase inhibitors as an approach towards novel antituberculars", Protein & Cell, XP009149386, vol. 1, No. 1, Jan. 2010, pp. 82-95; ISSN:1674-8018.

Lenka Zahajska, et al; "Synthesis and Antimycobacterial Activity of Pyridylmethylsulfanyl and Naphthylmethyl-sulfanyl Derivatives of Benzazoles, 1,2,4,-Triazole, and Pyridine-2-carbothioamide/-2-carbonitrile", Arch. Pharm. Pharm Med. Chem, vol. 337, Issue 10, pp. 549-555, Oct. 2004.

International Search Report; dated Jun. 27, 2011; PCT/IN2011/000172.

* cited by examiner 1 2 3 4

2 5

3 6

4 7

2 11

R ,
a = H, b = Me. c = t-bu, d = 4-nitrophenyl,
e = 4-methoxyphenyl, f = 4-chlorophenyl.

1 8 9 10

R ,
a = H, b = Me. c = t-bu, d = 4-nitrophenyl,
e = 4-methoxyphenyl, f = 4-chlorophenyl.

1, 2, 4-TRIAZOLE DERIVATIVES AND THEIR ANTI MYCOBACTERIAL ACTIVITY

FIELD OF THE INVENTION

The present invention relates to 1,2,4-triazole derivatives of general formula I and belong to a structural class of propargylated 1,2,4-triazolethiols, allylated 1,2,4-triazolethiols and their sulphones and corresponding 1,2,3-triazole derivatives, to selectively act against dormant pathogenic tuberculi bacilli.

General Formula I

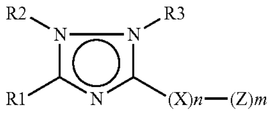

wherein,

X is sulfur(S) or a sulphone

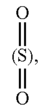

n, m represent independently an integer 0 or 1, with the provision that when ‘n’ is 1, ‘m’ is 1; R1 is hydrogen; C1-C6 linear or branched alkyl group optionally substituted with aryl group; halogen; or aryl group optionally substituted with —OCH3, halogen, and nitro; R2 and R3 are selected from the group consisting of hydrogen, C1-C6 alkyl optionally substituted with heterocyclic ring of 5 to 6 ring atoms containing one to three hetero atoms selected from oxygen, sulfur, nitrogen, which may be substituted with alkyl, arylalkyl, linear or branched alkenyl, substituted alkenyl, alkynyl, substituted alkynyl, or allyl or propargyl groups consisting of 1 to 6 carbon atoms; Z is C1-C6 alkyl optionally substituted with heterocyclic ring of 1 to 6 ring atoms, containing one to three hetero atoms selected from oxygen, sulfur, nitrogen, which may be substituted with arylalkyl, linear or branched alkenyl, substituted alkenyl, alkynyl, substituted alkynyl allyl or propargyl groups consisting of 1 to 6 carbon atoms;

with the provision that when ‘m’ is 1, and ‘n’ is zero; R1 is selected from the group consisting of hydrogen, halogen; C1-C6 linear or branched alkyl group optionally substituted with aryl group or aryl group optionally substituted with —OCH3, halogen, and nitro, R2 and R3 are selected from the group consisting of hydrogen, C1-C6 alkyl optionally substituted with heterocyclic ring of 5 to 6 ring atoms containing one to three hetero atoms selected from oxygen, sulfur, nitrogen, which may be substituted with alkyl, arylalkyl, linear or branched alkenyl, substituted alkenyl, alkynyl, substituted alkynyl, or allyl or propargyl groups consisting of 1 to 6 carbon atoms; Z is selected from the group consisting of halogen, C1-C6 linear or branched alkyl group optionally substituted with heterocyclic ring of 1 to 6 ring atoms, containing one to three hetero atoms selected from oxygen, sulfur, nitrogen, wherein the heterocyclic ring may further be substituted with halogen, alkyl, arylalkyl.

Present invention further relates to 1,2,4-triazole derivatives of general formula I and the representative compounds are:

Formula 1

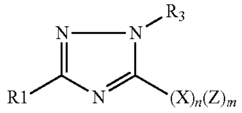

Formula 2

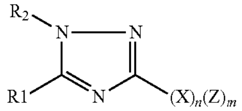

wherein R1, R2, R3, X, Z, n and m are same as described above.

Present invention further relates to 1,2,4-triazole derivatives of general formula I useful to selectively kill dormant pathogenic tuberculi bacilli.

BACKGROUND OF THE INVENTION

Tuberculosis (TB) is caused by *Mycobacterium tuberculosis* and remains as a leading cause of mortality worldwide. The treatment is complicated by a long-term administration of few antitubercular agents such as Rifampicin, Isoniazid, Ethambutol and Pyrazinamide in high dosage which intensifies drug side effects, and often results in the development of multidrug resistant strains and thus poor compliance from TB patients. In addition, the disease often attacks immunoaltered individuals. TB together with mycoses is the most common complication and the cause of death in AIDS patients. The failure of anti tubercular therapy is also related to migration of inhabitants from the areas with a higher incidence of TB to the regions with a favorable epidemiologic situation. Thus the current TB treatment is found to be not satisfactorily effective in the eradication of latent TB infection.

Triazoles are known for their antifungal, antiviral and plant growth regulatory activities but their antimycobacterial potential has gained importance only in recent years. Fluconazole and tebuconazole are known for their antimycobacterial activity but have non-specificity and higher MIC values. Moreover, they are not effective against dormant tubercle bacilli.

Further, azole antifungal derivatives such as fluconazole, hexaconazole which are N1 substituted 1,2,4-triazole compounds were found to be ergosterol biosynthesis inhibitors.

There is ample non-patented literature available on development of tubercular drugs as quoted below: References may be made to article “Arch Pharm Res Vol 27, No 5, 502-506, 2004” by Alireza Foroumadi, et al, which discloses two series of 2-(5-nitro-2-furyl)- and 2-(1-methyl-5-nitro-1H-imidazol-2-yl)-5-propyl, allyl and propargyl)thio-1,3,4-thiadiazoles and 2-(5-nitro-2-furyl)- and 2-(1-methyl-5-nitro-1H-imidazol-2-yl)-5-(nitrobenzyl)thio-1,3,4-thiadiazole derivatives which were evaluated against *Mycobacterium tuberculosis*. The compounds 2-(1-Methyl-5-nitro-1H-imidazol-2-yl)-5-(n-propyl)thio-1,3,4-thiadiazole, 2-(5-nitro-2-furyl)-5-(2-propynyl)thio-1,3,4-thiadiazole, 2-(5-nitro-2-furyl)-5-(2-nitrobenzyl)thio-1,3,4-thiadiazole, 2-(5-nitro-2-furyl)-5-(3-nitrobenzyl)thio-1,3,4-thiadiazole, 2-(5-nitro-2furyl)-5-(4-nitrobenzyl)thio-1,3,4-thiadiazole displayed significant inhibition effects (90%) in the primary screening (MIC>>6.25 μg/mL) against *M. tuberculosis* H37Rv in the BACTEC 12B medium, using the BACTEC 460 radiometric system.

References may be made to *Journal “Enzyme Inhibition and Medicinal Chemistry*, Volume 22, Issue 4 Aug. 2007, pages 511-516” by Gulhan Turan-et al where it discloses another study, wherein a series of 4-arylidenamino-4H-1,2,4-triazole-3-thiol derivatives were synthesized by reaction of 4-amino-4H-1,2,4-triazoles-3-thiol with the respective aldehydes and were evaluated for anti tuberculosis activity against *Mycobacterium tuberculosis* H37Rv (ATCC 27294), using the BACTEC 460 radiometric system and BACTEC 12B medium. Compounds showed an activity at 6.25 μg/mL with 87 percentage inhibition. In another article, a series of N-{4-[(4-amino-5-sulfanyl-4H-1,2,4-triazol-3-yl)methyl]-1,3-thiazol-2-yl}-2-substituted amide derivatives were synthesized and evaluated for their preliminary in vitro antitubercular activity against *Mycobacterium tuberculosis* H37Rv strain by the MABA assay method. Compounds such as N-(5-{[((1E)-1-aza-2-phenylvinyl)carbamoyl]methylthio}-3-{[2-(acetylamino)(1,3-thiazol-4-yl])methyl}(1,2,4-triazol-4-yl))-acetamide, N-{4-[(5-{[((1E)-1-aza-2-phenylvinyl)carbamoyl]methylthio}-4-acetylamino(1,2,4-triazol-3-yl))methyl](1,3-thiazol-2-yl)}-2-chloroacetamide and N-(5-{[((1E)-1-aza-2-phenylvinyl)carbamoyl]methylthio}-3-{[2-(phenylamino)(1,3-thiazol-4-yl])methyl}(1,2,4-triazol-4-yl))-acetamide exhibited more than 94% inhibition at 12.5 μg/mL. [Mahendra Shiradkar, et al, General Papers, ARKIVOC 2006 (xiv) 141-154].

A series of 5-amino-4-(5-arylpyrazol-3-yl)-1-(3/4-nitrophenyl)-1,2,3-triazoles that have been synthesized by the base-catalysed condensation of 3/4-nitrophenyl azides with 5-aryl-3-cyanomethylpyrazoles is disclosed as potential anti-invasive and antimycobacterial agents by Ajay Kumar, et al in Indian Journal of Chemistry Sect. B Organic Chemistry including Medicinal Chemistry VOL. 42B NUMBER 8 Aug. 2003 Paper 1950.

References may be made to article "Structural elucidation of propargylated products of 3-substituted-1,2,4-triazole-5-thiols by NMR techniques in Magnetic Resonance Chemistry, 2008 December; 46(12):1168-74" by Chaudhary P M, Chavan S R, Kavitha M having DOI 10.1002/mrc.2307, which discloses synthesis and characterization of mono S-propargyl and S,N-dipropargyl regioisomers, arising from N1/N2 substitution to study their biological activity.

References may be made to Journal "European Journal of Medicinal Chemistry Volume 43, Issue 2, February 2008, Pages 381-392" by Ilkay Küçükgüzel, et al, which discloses heterocyclic derivatives of 5-[(4-aminophenoxy)methyl]-4-alkyl/aryl-2,4-dihydro-3H-1,2,4-triazole-3-ylthiones and N-alkyl/aryl-N'-{4-[(4-alkyl/aryl-5-thioxo-4,5-dihydro-1H-1,2,4-triazol-3-yl)methoxy]phenyl}thioureas.

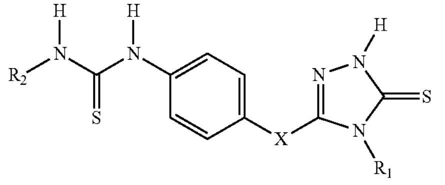

The above compound showed 79% inhibition against *M. tuberculosis* H37Rv where $R_1$ is $CH_2CH{=}CH_2$, $R_2$ is $C_6H_5$, X is $—O—CH_2—$.

References may be made to Journal "Indian Journal of Chemistry Sect. B Organic Chemistry including Medicinal Chemistry VOL. 42B No. 8 August 2003 Paper 2010" by B Shivarama Holla, B Veerendra, M K Shivananda & N Sucheta Kumari, which discloses synthesis and antibacterial activity of Schiff bases and bis-triazolothiadiazoles derived from bis-1,2,4-triazole.

References may be made to Article "UDC 547.791,796.07" by L. I. Vereshchagin, et al, which discloses a number of corresponding 1- and 2-propargylazoles which were obtained by propargylation of 5-substituted tetrazoles and 1,2,3-triazoles with various degrees of substitution. These polyazole structures with a system of two to five uncondensed azole rings were synthesized by the reaction of 1- and 2-propargyl azoles with organic azides, diazides, and azoles, as well as by oxidative dimerization. The uncondensed polynitrogenous heterocyclic compounds were shown to exhibit pesticidal activity.

There still remains a need to develop antitubercular compounds to overcome the limitations encountered in the tuberculosis drug discovery programme as evident from the prior art.

Thus the present inventors felt a need to develop novel azole derivatives which are capable of inhibiting the growth of dormant tuberculi bacilli such as *Mycobacterium bovis* BCG and *M. tuberculosis* completely.

Objective of the Invention

The main object of the present invention is to provide 1,2,4-triazole derivatives of general Formula I.

Another objective of the present invention is to provide 1,2,4-triazole derivatives specifically belonging to a structural class of propargylated 1,2,4-triazolethiols and their sulphones and corresponding 1,2,3-triazole derivatives to selectively kill pathogenic *M. tuberculosis.*

Another objective of the present invention is to provide process for the preparation of 1,2,4-triazole derivatives of Formula I and II which are, effectively used against dormant tubercle bacilli, *Mycobacterium bovis* BCG and *Mycobacterium tuberculosis* H37Ra.

SUMMARY OF THE INVENTION

Figure 1:
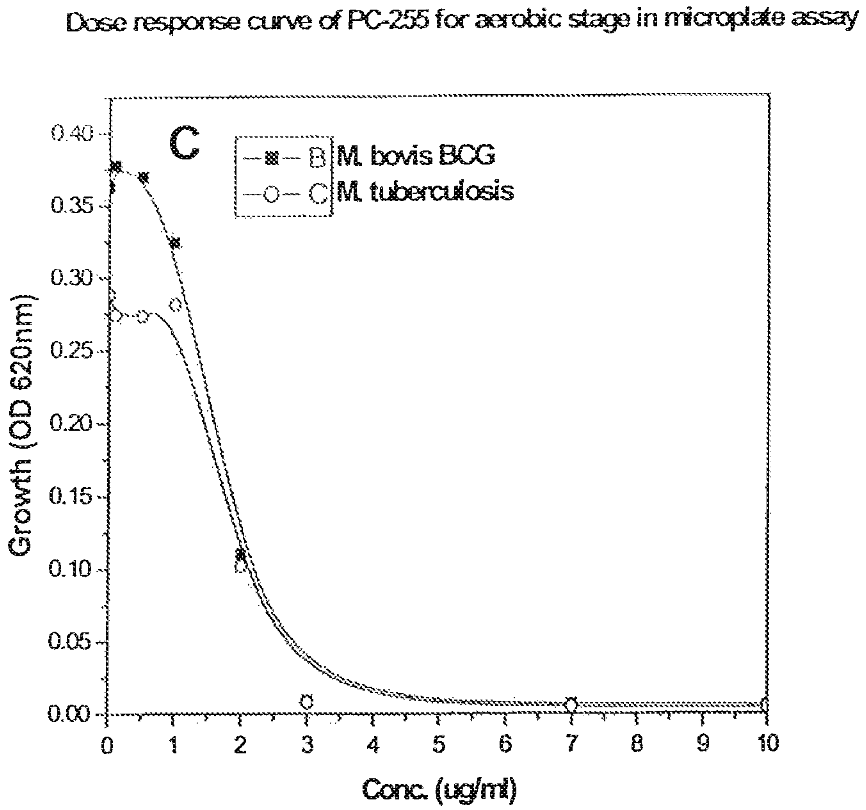
FIG. 1 is a graph showing dose response effect of compound 4f on the growth of *M. bovis* BCG and *M. tuberculosis* H37Ra.
Figure 2:
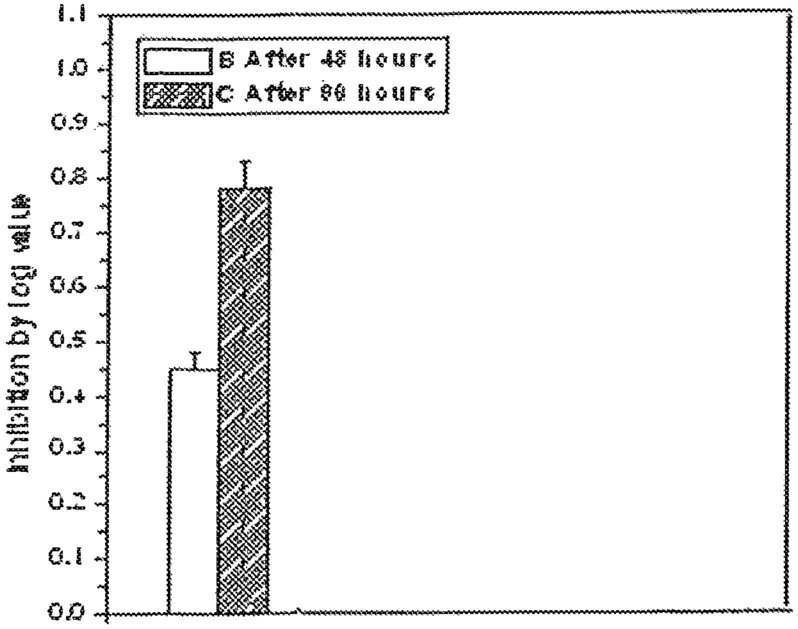
FIG. 2 is a graph showing effect of compound 4f at MIC of aerobic stage on the viability of *M. tuberculosis* H37Ra.
Figure 3:
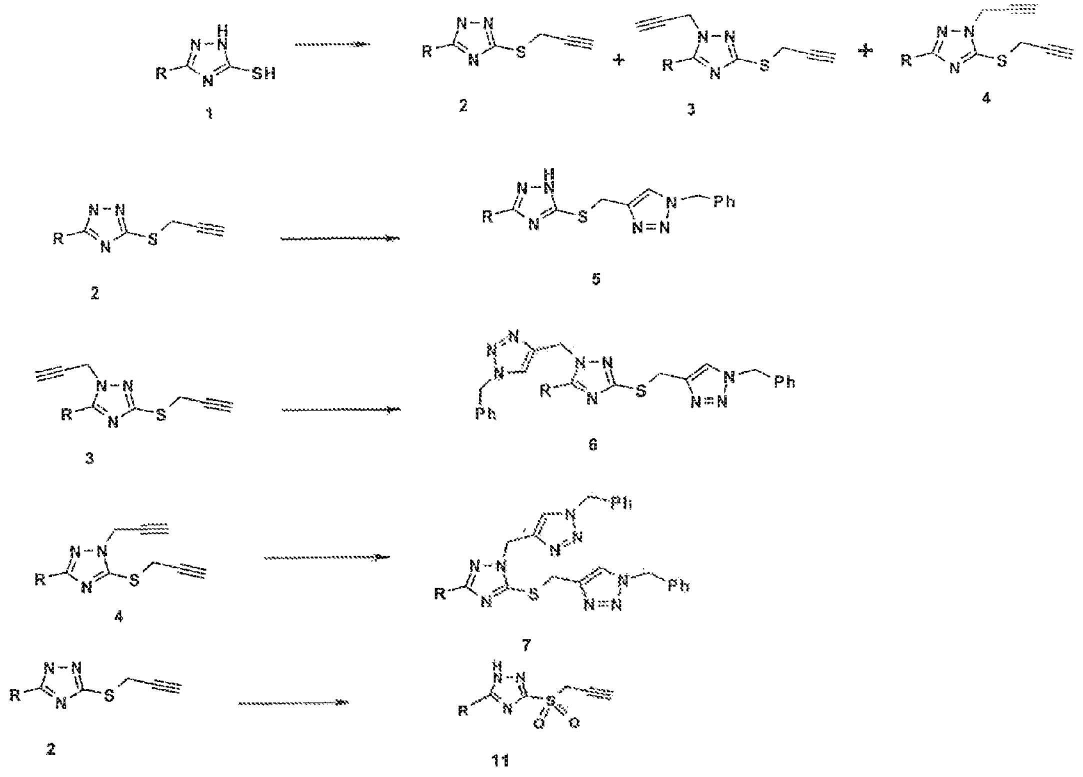
FIG. 3 represents Scheme 1, the flow diagram for the preparation of compounds 2-7 and 11.
Figure 4:
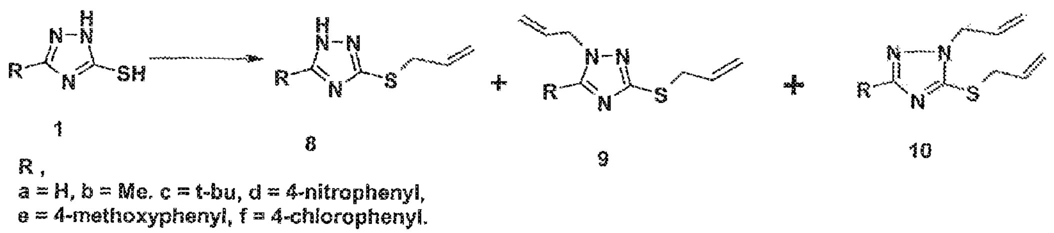
FIG. 4 represents Scheme 2, the flow diagram for the preparation of compounds 8-10.

Accordingly, present invention provides Compounds of General Formula I,

General Formula I

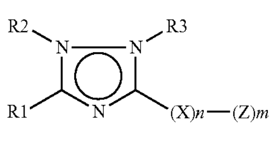

wherein,

X is sulfur(S) or a sulphone

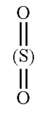

n, m represent independently an integer 0 or 1, with the provision that when 'n' is 1, 'm' is 1; R1 is hydrogen; C1-C6 linear or branched alkyl group optionally substituted with aryl group; halogen; or aryl group optionally substituted with —OCH3, halogen, and nitro; R2 and R3 are selected from the group consisting of hydrogen, C1-C6 alkyl optionally substituted with heterocyclic ring of 5 to 6 ring atoms containing one to three hetero atoms selected from oxygen, sulfur, nitrogen, which may be substituted with alkyl, arylalkyl, linear or branched alkenyl, substituted alkenyl, alkynyl, substituted alkynyl, or allyl or propargyl groups consisting of 1 to 6 carbon atoms; Z is C1-C6 alkyl optionally substituted with heterocyclic ring of 1 to 6 ring atoms, containing one to three hetero atoms selected from oxygen, sulfur, nitrogen, which may be substituted with arylalkyl, linear or branched alkenyl, substituted alkenyl, alkynyl, substituted alkynyl allyl or propargyl groups consisting of 1 to 6 carbon atoms;

with the provision that when ‘m’ is 1, and ‘n’ is zero; R1 is selected from the group consisting of hydrogen, halogen; C1-C6 linear or branched alkyl group optionally substituted with aryl group or aryl group optionally substituted with —OCH3, halogen, and nitro, R2 and R3 are selected from the group consisting of hydrogen, C1-C6 alkyl optionally substituted with heterocyclic ring of 5 to 6 ring atoms containing one to three hetero atoms selected from oxygen, sulfur, nitrogen, which may be substituted with alkyl, arylalkyl, linear or branched alkenyl, substituted alkenyl, alkynyl, substituted alkynyl, or allyl or propargyl groups consisting of 1 to 6 carbon atoms; Z is selected from the group consisting of halogen, C1-C6 linear or branched alkyl group optionally substituted with heterocyclic ring of 1 to 6 ring atoms, containing one to three hetero atoms selected from oxygen, sulfur, nitrogen, wherein the heterocyclic ring may further be substituted with halogen, alkyl, arylalkyl.

In an embodiment of the present invention, representative compounds comprising:

1-benzyl-4-((1-((1-benzyl-1H-1,2,3-triazol-4-yl)methyl)-3-(4-chlorophenyl)-1H-1,2,4-triazol-5-ylthio)methyl)-1H-1,2,3-triazole 3f;
3-(allylthio)-5-methyl-1H-1,2,4-triazole 4b;
3-(allylthio)-5-tert-butyl-1H-1,2,4-triazole 4c;
3-(allylthio)-5-(4-methoxyphenyl)-1H-1,2,4-triazole 4e;
3-(allylthio)-5-(4-chlorophenyl)-1H-1,2,4-triazole 4f;
1-allyl-3-(allylthio)-1H-1,2,4-triazole 5a;
1-allyl-3-(allylthio)-5-(4-methoxyphenyl)-1H-1,2,4-triazole 5e;
1-allyl-3-(allylthio)-5-(4-chlorophenyl)-1H-1,2,4-triazole 5f;
1-allyl-5-(allylthio)-1H-1,2,4-triazole 6a;
1-allyl-5-(allylthio)-3-(4-methoxyphenyl)-1H-1,2,4-triazole 6e;
5-(prop-2-ynylsulfonyl)-1H-1,2,4-triazole 7a;
3-tert-butyl-5-(prop-2-ynylsulfonyl)-1H-1,2,4-triazole 7c;
3-(4-nitrophenyl)-5-(prop-2-ynylsulfonyl)-1H-1,2,4-triazole 7d;
3-(4-methoxyphenyl)-5-(prop-2-ynylsulfonyl)-1H-1,2,4-triazole 7e;
3-(4-chlorophenyl)-5-(prop-2-ynylsulfonyl)-1H-1,2,4-triazole 7f;
1-allyl-3-tert-butyl-5-(prop-2-ynylthio)-1H-1,2,4-triazole 8a;
1-allyl-5-tert-butyl-3-(prop-2-ynylthio)-1H-1,2,4-triazole 8b;
5-(allylthio)-3-tert-butyl-1-(prop-2-ynyl)-1H-1,2,4-triazole 8c;
3-(allylthio)-5-tert-butyl-1-(prop-2-ynyl)-1H-1,2,4-triazole 8d;
3,5-dibromo-1-(prop-2-ynyl)-1H-1,2,4-triazole 11a;
1-allyl-5-methyl-3-(prop-2ynylthio)-1H-1,2,4-triazole 10b;
1-allyl-3-(prop-2-ynlthio)-1H-1,2,4-triazole 9b;
1-allyl-5-(prop-2-ynylthio)-1H-1,2,4-triazole 9a;

In yet another embodiment of the present invention, structural formula of the representative compound are:

2a

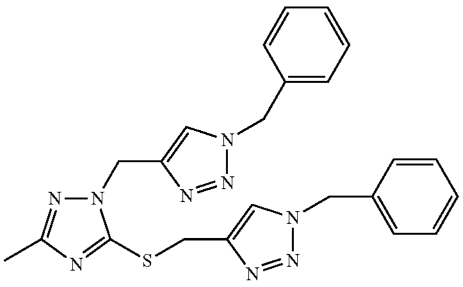

3e

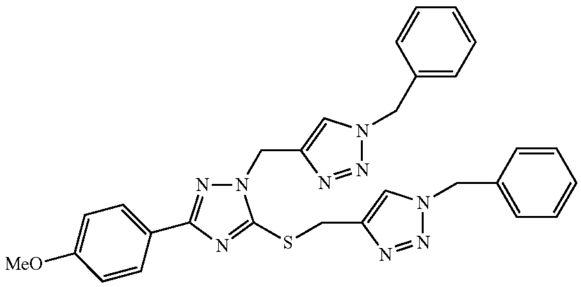

4a

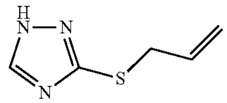

4b

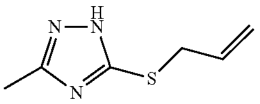

4c

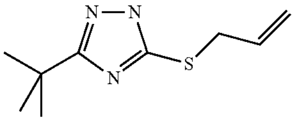

4e

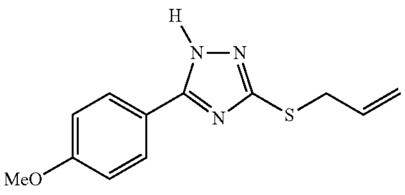

4f

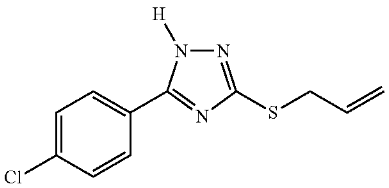

6a

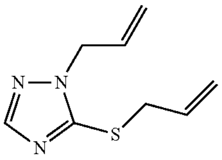

-continued
5e
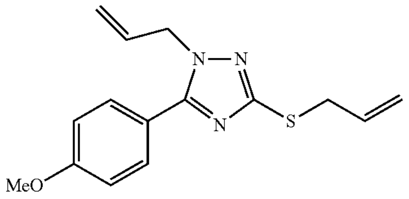
5f
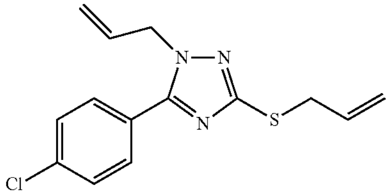
5a
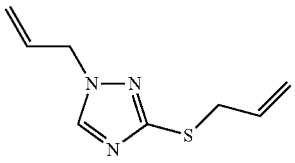
6e
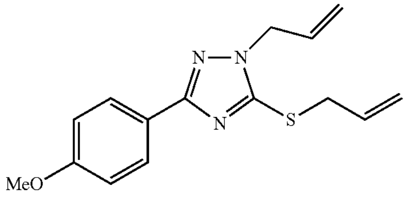
7b
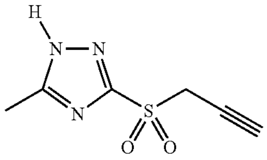
7c
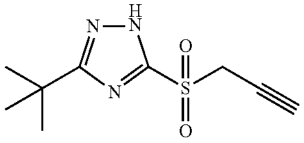
7d
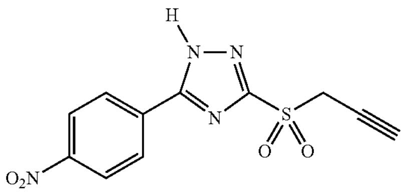
7e
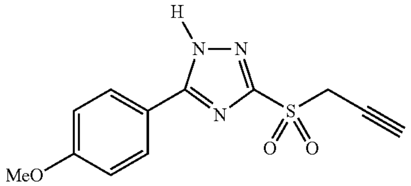
-continued
7f
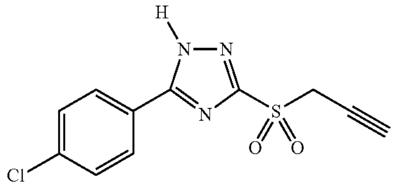
8a
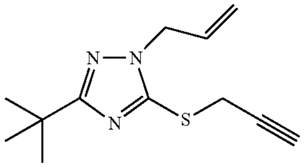
8b
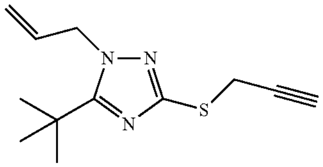
8c
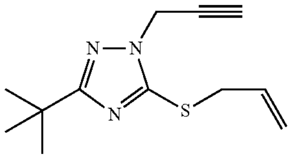
8d
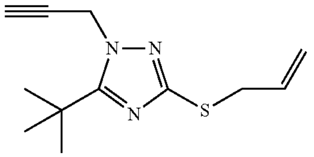
9b
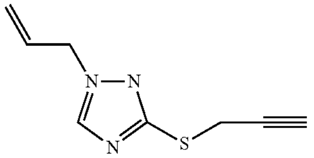
10a
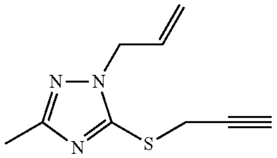
10b
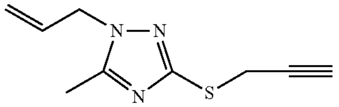
11a
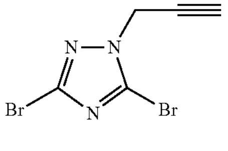

In yet another embodiment of the present invention, said compounds are antitubercular and are active against actively growing as well as dormant bacilli of *Mycobacterium bovis* BCG and *Mycobacterium tuberculosis* H37Ra.

In yet another embodiment of the present invention, a process for the preparation of compounds of General formula I and the said process comprising the steps of:

i. reacting 5-substituted 1,2,4-triazole-3-thiols with propargyl bromide, in presence of $K_2CO_3$ at temperature in the range of 25 to 30° C. to give S-monopropargylated and N,S-dipropargylated products;
ii. oxidizing S-monopropargylated compounds to give sulphone derivatives of formula 7a-f;
iii. alternately, treating the terminal alkyne group of all the S-monopropargylated and NS-dipropargylated 1,2,4-triazole thiols with benzyl azide in presence of Cu(I) catalyst at temperature in the range of 25 to 30° C. to form 1,2,3-triazole derivatives of formula 1a-1c, 2a-2c, 2e, 2f, 3a-3f.

DETAILED DESCRIPTION OF THE INVENTION

Present invention provides 1, 2, 4 triazole derivatives as anti-tubercular compounds of general formula I General Formula I

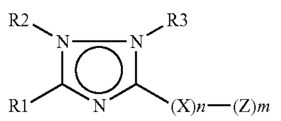

wherein,
X is sulfur(S) or a sulphone

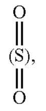

n, m represent independently an integer 0 or 1, with the provision that when 'n' is 1, 'm' is 1; R1 is hydrogen; C1-C6 linear or branched alkyl group optionally substituted with aryl group; halogen; or aryl group optionally substituted with —OCH3, halogen, and nitro; R2 and R3 are selected from the group consisting of hydrogen, C1-C6 alkyl optionally substituted with heterocyclic ring of 5 to 6 ring atoms containing one to three hetero atoms selected from oxygen, sulfur, nitrogen, which may be substituted with alkyl, arylalkyl, linear or branched alkenyl, substituted alkenyl, alkynyl, substituted alkynyl, or allyl or propargyl groups consisting of 1 to 6 carbon atoms; Z is C1-C6 alkyl optionally substituted with heterocyclic ring of 1 to 6 ring atoms, containing one to three hetero atoms selected from oxygen, sulfur, nitrogen, which may be substituted with arylalkyl, linear or branched alkenyl, substituted alkenyl, alkynyl, substituted alkynyl allyl or propargyl groups consisting of 1 to 6 carbon atoms;

with the provision that when 'm' is 1, and 'n' is zero; R1 is selected from the group consisting of hydrogen, halogen; C1-C6 linear or branched alkyl group optionally substituted with aryl group or aryl group optionally substituted with —OCH3, halogen, and nitro, R2 and R3 are selected from the group consisting of hydrogen, C1-C6 alkyl optionally substituted with heterocyclic ring of 5 to 6 ring atoms containing one to three hetero atoms selected from oxygen, sulfur, nitrogen, which may be substituted with alkyl, arylalkyl, linear or branched alkenyl, substituted alkenyl, alkynyl, substituted alkynyl, or allyl or propargyl groups consisting of 1 to 6 carbon atoms; Z is selected from the group consisting of halogen, C1-C6 linear or branched alkyl group optionally substituted with heterocyclic ring of 1 to 6 ring atoms, containing one to three hetero atoms selected from oxygen, sulfur, nitrogen, wherein the heterocyclic ring may further be substituted with halogen, alkyl, arylalkyl.

Present invention provides compounds of general formula I wherein representative compounds of general formula I are:

Formula 1

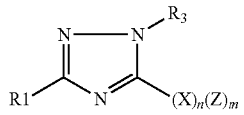

Formula 2

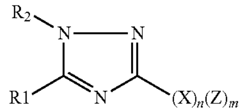

wherein R1, R2, R3, X, Z, n and m are as described above.

Present invention describes process for preparation of the compounds of Formula I and II as depicted in Scheme 1 wherein R=R1, wherein R1 is as described above.

Accordingly, the general process for the preparation of Formula I and II comprises of the following steps:

(a) reacting 5-substituted 1,2,4-triazole-3-thiols with propargyl bromide in presence of $K_2CO_3$ at room temperature to give S-monopropargylated and N,S-dipropargylated products; and
(b) oxidizing S-monopropargylated compounds to give sulphone derivatives (7a-f)).
(c) alternately, treating the terminal alkyne group of all the S-monopropargylated and NS-dipropargylated 1,2,4-triazole thiols with benzyl azide in presence of Cu(I) catalyst at room temperature to form 1,2,3-triazole derivatives 1a-1c, 2a-2c, 2e, 2f, 3a-3f.

The propargylated derivatives are purified by flash column chromatography.

Allylation was carried out on these thiols as depicted in Scheme 2 to yield various regioisomers which were tested for their antitubercular activity.

Total of 50 derivatives (Table 1) were synthesized using the method illustrated in Scheme 1 and Scheme 2.

The anti tubercular activity of the compounds of the present invention is observed by in-vitro experiment as depicted in table 1 below.

The antimycobacterial activity against dormant bacilli was observed at concentration of less than 100 μg/ml in in-vitro culture conditions.

TABLE1

In-vitro antimycobacterial activity of triazole derivatives against *M. bovis* BCG.

| S. N. | Chemical Structure | compound | Spectral data | Antimycobacterial activity[a] % inhibition at 100 μg/ml Aerobic/Active stage | Anearobic/Dormant stage |
|---|---|---|---|---|---|
| 1. | 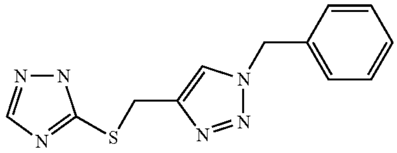 [SMILES: c1ccc(Cn2cc(CSc3ncn[nH]3)nn2)cc1] | 1a | $^1$H NMR δ 8.06 (s, 1H), 7.42 (s, 1H), 7.18-7.27 (m, 5H), 5.37 (s, 2H) 4.29 (s, 2H); | 03 | 04 |
| 2. | 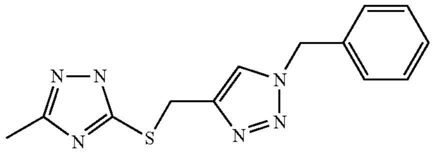 [SMILES: Cc1n[nH]c(SCc2cn(Cc3ccccc3)nn2)n1] | 1b | $^1$H NMR δ 7.51 (s, 1H), 7.36-7.20 (m, 5H), 5.48 (s, 2H), 4.38 (s, 2H), 2.43 (s, 3H); | 10 | 14 |
| 3. | 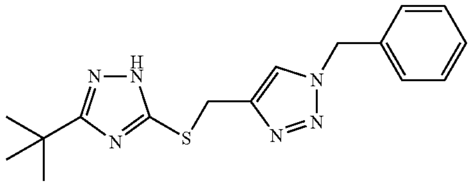 [SMILES: CC(C)(C)c1n[nH]c(SCc2cn(Cc3ccccc3)nn2)n1] | 1c | $^1$H NMR δ 7.42 (s, 1H), 7.43 (m, 5H), 5.39 (s, 2H), 4.29 (s, 2H), 1.27 (s, 9H); | 03 | 11 |
| 4. | 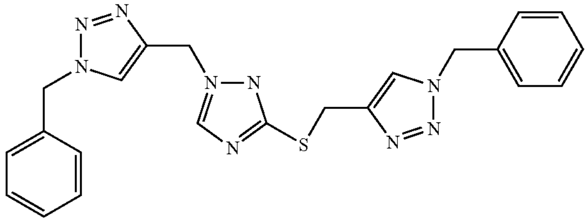 | 2a | $^1$H NMR δ 8.06 (s, 1H), 7.59 (s, 1H), 7.45 (s, 1H), 7.25 (m, 10H), 5.49 (s, 2H), 5.42 (s, 2H), 5.33 (s, 2H), 4.36 (s, 2H); | 11 | 18 |
| 5. | 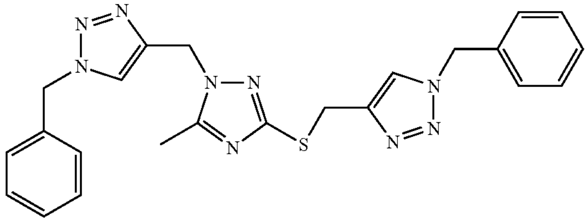 [SMILES: Cc1nc(SCc2cn(Cc3ccccc3)nn2)nn1Cc1cn(Cc2ccccc2)nn1] | 2b | $^1$H NMR δ 7.52 (s, 1H), 7.38 (s, 1H), 7.11-7.30 (m, 10H), 5.41 (s, 2H), 5.35 (s, 2H), 5.18 (s, 2H), 4.26 (s, 2H), 2.39 (s, 3H); | 08 | 12 |
| 6. | 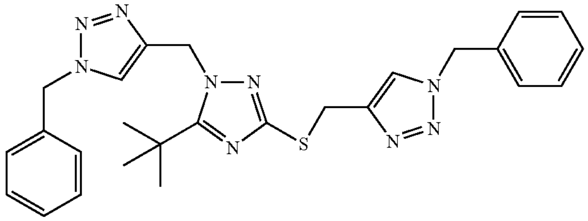 [SMILES: CC(C)(C)c1nc(SCc2cn(Cc3ccccc3)nn2)nn1Cc1cn(Cc2ccccc2)nn1] | 2c | $^1$H NMR δ 7.63 (s, 1H), 7.43 (s, 1H), 7.10-7.3 (m, 10H), 5.44 (s, 2H), 5.4 (s, 2H), 5.38 (s, 2H), 4.29 (s, 2H), 1.43 (s, 9H); | 08 | 15 |
| 7. | 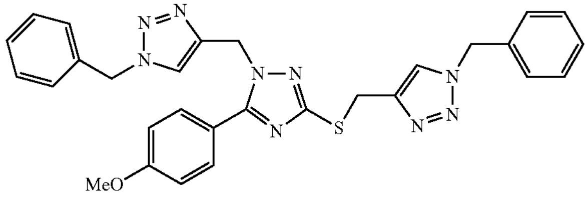 [SMILES: COc1ccc(-c2nc(SCc3cn(Cc4ccccc4)nn3)nn2Cc2cn(Cc3ccccc3)nn2)cc1] | 2e | $^1$H NMR δ 7.63 (s, 1H), 7.67 (s, 2H), 7.47 (s, 1H), 7.29 (m, 9H), 7.19 (bs, 2H), 6.98 (d, 2H, J = 8 Hz), 5.49 (s, 2H), 5.41 (s, 2H), 5.36 (s, 2H), 4.39 (s, 2H), 3.84 (s, 3H); | 01 | 08 |

TABLE1-continued

In-vitro antimycobacterial activity of triazole derivatives against *M. bovis* BCG.

| S. N. | Chemical Structure | compound | Spectral data | Antimycobacterial activity[a] % inhibition at 100 µg/ml Aerobic/Active stage | Anearobic/Dormant stage |
|---|---|---|---|---|---|
| 8. | 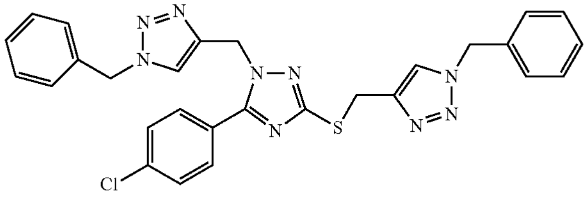 [SMILES: Clc1ccc(-c2nc(SCc3cn(Cc4ccccc4)nn3)nn2Cc2cn(Cc3ccccc3)nn2)cc1] | 2f | $^1$H NMR δ 7.71 (s, 1H), 7.72 (s, 1H), 7.68 (s, 1H), 7.47-7.43 (m, 8H), 5.49 (s, 2H), 5.41 (s, 2H), 5.34 (s, 2H), 4.39 (s, 2H); | 21 | 17 |
| 9. | 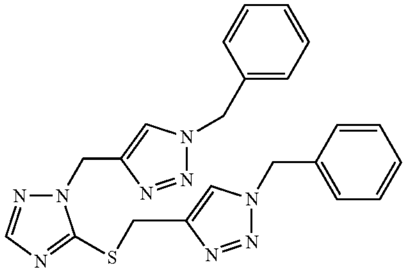 [SMILES: c1ccc(Cn2cc(CSc3ncnn3Cc3cn(Cc4ccccc4)nn3)nn2)cc1] | 3a | $^1$H NMR δ 7.9 (s, 1H), 7.59 (s, 1H), 7.45 (s, 1H), 7.20 (m, 10H), 5.49 (s, 2H), 5.35 (s, 2H), 5.2 (s, 2H), 4.4 (s, 2H) | 08 | 03 |
| 10 | 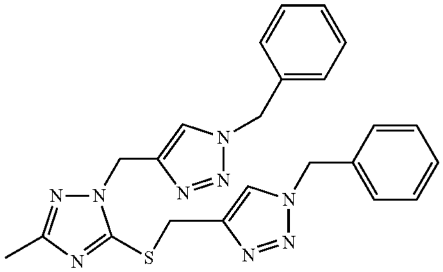 [SMILES: Cc1nc(SCc2cn(Cc3ccccc3)nn2)n(Cc2cn(Cc3ccccc3)nn2)n1] | 3b | $^1$H NMR δ 7.39 (s, 1H), 7.36 (s, 1H), 7.32-7.1 (m, 6H), 7.24-7.20 (m, 2H), 7.6-7.10 (m, 2H), 5.43 (s, 2H), 5.41 (s, 2H), 5.19 (s, 2H), 4.39 (s, 2H), 2.23 (s, 3H); | 85 | 76 |
| 11 | 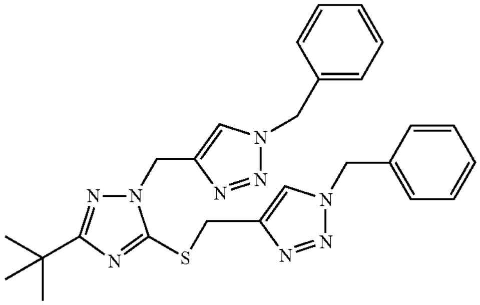 [SMILES: CC(C)(C)c1nc(SCc2cn(Cc3ccccc3)nn2)n(Cc2cn(Cc3ccccc3)nn2)n1] | 3c | $^1$H NMR δ 7.32 (s, 1H), 7.29 (s, 1H), 7.04-7.25 (m, 10H,), 5.38 (s, 2H), 5.34 (s, 2H), 5.15 (s, 2H), 4.33 (s, 2H), 1.16 (s, 9H); | 10 | 13 |
| 12 | 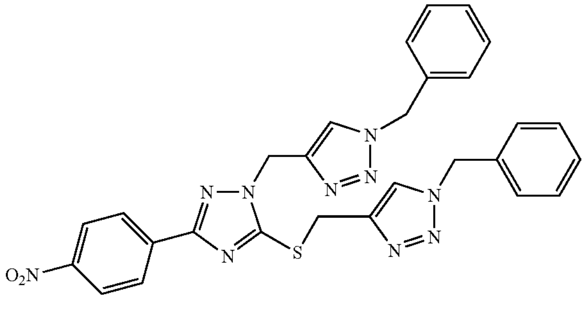 [SMILES: O=[N+]([O-])c1ccc(-c2nc(SCc3cn(Cc4ccccc4)nn3)n(Cc3cn(Cc4ccccc4)nn3)n2)cc1] | 3d | | 13 | 11 |

TABLE1-continued

In-vitro antimycobacterial activity of triazole derivatives against *M. bovis* BCG.

| S. N. | Chemical Structure | compound | Spectral data | Antimycobacterial activity[a] % inhibition at 100 μg/ml Aerobic/Active stage | Anearobic/Dormant stage |
|---|---|---|---|---|---|
| 13 | 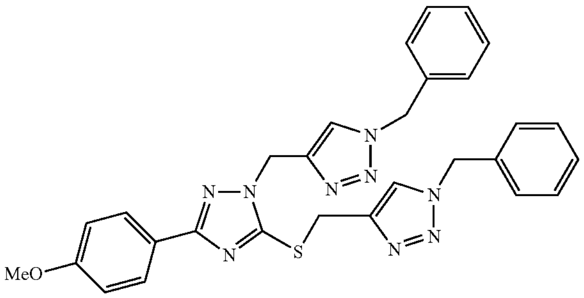 [SMILES: COc1ccc(-c2nc(SCc3cn(Cc4ccccc4)nn3)n(Cc3cn(Cc4ccccc4)nn3)n2)cc1] | 3e | $^{1}$H NMR δ 7.84 (d, 2H, J = 8 Hz), 7.23-7.10 (m, 12H), 6.83 (d, 2H, J = 8 Hz), 5.38 (s, 2H), 5.32 (s, 2H), 5.24 (s, 2H), 4.43(s, 2H), 3.77 (s, 3H); | 86 | 82 |
| 14 | 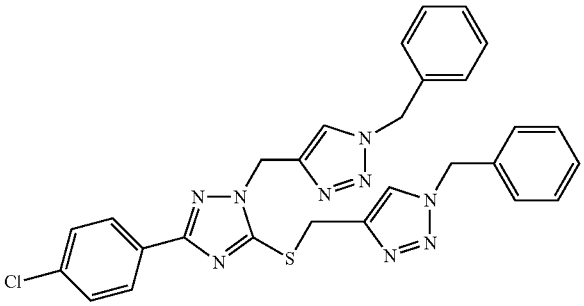 [SMILES: Clc1ccc(-c2nc(SCc3cn(Cc4ccccc4)nn3)n(Cc3cn(Cc4ccccc4)nn3)n2)cc1] | 3f | $^{1}$H NMR δ 7.84 (s, 1H), 7.80 (s, 1H), 7.30-7.10 (m, 12H), 7.04 (m, 2H), 5.38 (s, 2H), 5.32 (s, 2H), 5.23 (s, 2H), 4.42 (s, 2H); | 31 | 04 |
| 15 | 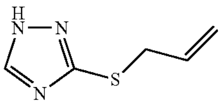 | 4a | $^{1}$H NMR δ 8.17 (s, 1H), 5.91 (m, 1H), 5.24 (d, 1H), 5.075 (s, 1H), 3.75 (dd, 1H). | 51 | 32 |
| 16 | 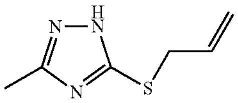 | 4b | | 98 | 97 |
| 17 | 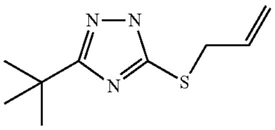 | 4c | $^{1}$H NMR δ 5.87 (m, 1H), 4.79 (d, 2H), 3.63 (d, 2H), 1.30 (s, 9H) | 57 | 39 |
| 18 | 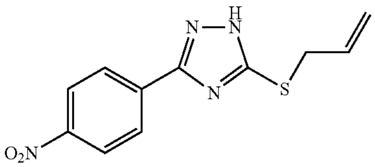 [SMILES: C=CCSc1nc(-c2ccc([N+](=O)[O-])cc2)n[nH]1] | 4d | $^{1}$H NMR δ 8.27 (m, 4H), 6.02 (m, 1H), 5.36 (m, 2H), 4.86 (dd, 2H) | 25 | 14 |
| 19 | 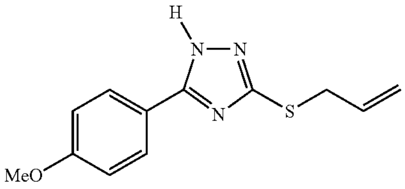 [SMILES: C=CCSc1n[nH]c(-c2ccc(OC)cc2)n1] | 4e | $^{1}$H NMR δ 8.01 (d, 2H), 6.91 (d, 2H), 6.01 (m, 1H), 5.35 (m, 2H), 4.78 (m, 2H), 3.85 (s, 3H) | 94 | 93 |

TABLE1-continued

In-vitro antimycobacterial activity of triazole derivatives against *M. bovis* BCG.

| S. N. | Chemical Structure | com-pound | Spectral data | Antimycobacterial activity[a] % inhibition at 100 μg/ml Aerobic/ Active stage | Anearobic/ Dormant stage |
|---|---|---|---|---|---|
| 20 | 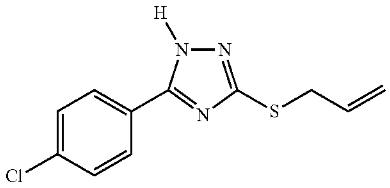 [SMILES: C=CCSc1n[nH]c(-c2ccc(Cl)cc2)n1] | 4f | $^1$H NMR δ 8.04 (d, 2H), 7.37 (d, 2H), 6.03 (m, 1H), 5.35 (m, 2H), 4.81 (m, 2H) | 98 | 91 |
| 21 | 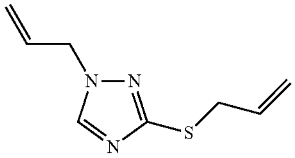 | 5a | $^1$H NMR δ 7.85 (s, 1H), 5.87 (m, 2H), 5.17 (m, 4H), 4.68(d, 2H), 3.80 (d, 2H) | 58 | 42 |
| 22 | 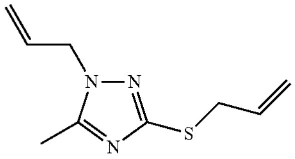 | 5b | | 25 | 15 |
| 23 | 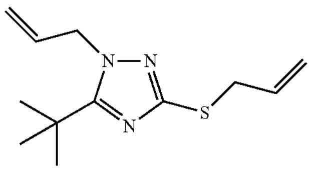 [SMILES: C=CCSc1nc(C(C)(C)C)n(CC=C)n1] | 5c | $^1$H NMR δ 5.87 (m, 2H), 5.17 (m, 4H), 4.75 (d, 2H), 3.63 (d, 2H), 1.28 (s, 9H) | 45 | 36 |
| 24 | 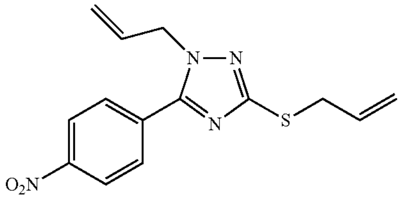 [SMILES: C=CCSc1nc(-c2ccc([N+](=O)[O-])cc2)n(CC=C)n1] | 5d | $^1$H NMR δ 8.20 (m, 4H), 5.90 (d, 2H), 5.16 (m, 4H), 4.68 (m, 2H), 3.90 (d, 2H) | 15 | 18 |
| 25 | 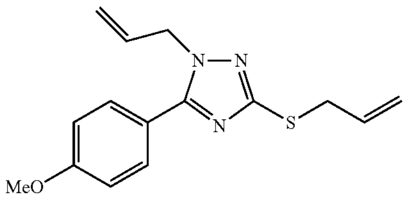 [SMILES: C=CCSc1nc(-c2ccc(OC)cc2)n(CC=C)n1] | 5e | $^1$H NMR δ 8.01 (d, 2H), 6.93 (d, 2H), 5.94 (m, 2H), 5.25 (M, 4H), 4.78 (m, 2H), 3.86 (d, 2H), 3.83 (s, 3H) | 89 | 84 |
| 26 | 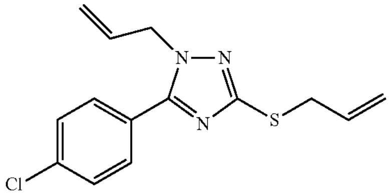 [SMILES: C=CCSc1nc(-c2ccc(Cl)cc2)n(CC=C)n1] | 5f | $^1$H NMR δ 8.04 (d, 2H), 7.37 (d, 2H), 3.95 (d J = 8 Hz, 2H ), 4.76 (d J = 6 Hz, 2H), 5.2 (m, 4H), 5.94 (m, 2H) | 94 | 91 |

TABLE1-continued

In-vitro antimycobacterial activity of triazole derivatives against *M. bovis* BCG.

| S. N. | Chemical Structure | com-pound | Spectral data | Antimycobacterial activity[a] % inhibition at 100 μg/ml Aerobic/Active stage | Anearobic/Dormant stage |
|---|---|---|---|---|---|
| 27 | 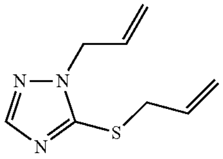 | 6a | $^1$H NMR δ 7.97 (s, 1H), 5.93 (m, 2H), 5.89 (s, 1H), 5.17 (m, 4H), 4.69 (d, 2H), 3.71 (d, 2H) | 65 | 60 |
| 28 | 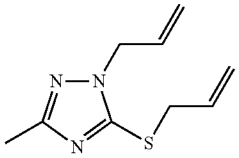 | 6b | $^1$H NMR δ 5.83 (m, 2H), 5.13 (m, 4H), 4.59 (d, 2H), 3.76 (d, 2H), 2.31 (s, 3H) | 22 | 10 |
| 29 | 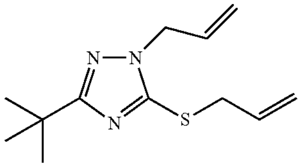 [SMILES: C=CCSc1nc(C(C)(C)C)nn1CC=C] | 6c | $^1$H NMR δ 5.87 (m, 2H), 5.17 (m, 4H), 4.64 (d, 2H), 3.73 (d, 2H), 1.28 (s, 9H) | 30 | 33 |
| 30 | 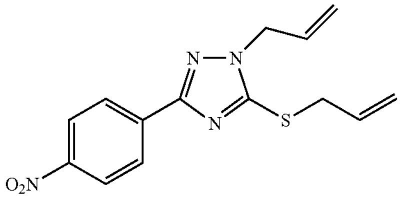 [SMILES: C=CCSc1nc(-c2ccc([N+](=O)[O-])cc2)nn1CC=C] | 6d | $^1$H NMR δ 8.25 (m, 4H), 5.93 (d, 2H), 5.26 (m, 4H), 4.78 (m, 2H), 3.90 (d, 2H) | 40 | 12 |
| 31 | 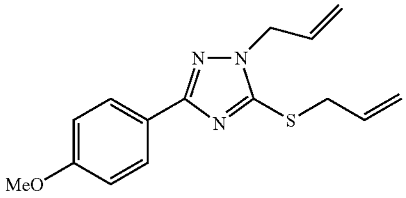 [SMILES: C=CCSc1nc(-c2ccc(OC)cc2)nn1CC=C] | 6e | $^1$H NMR δ 8.01 (d, 2H), 6.93 (d, 2H), 6.01 (m, 2H), 5.25 (m, 4H), 4.74 (m, 2H), 3.83 (s, 3H), 3.77 (d, 2H) | 88 | 83 |
| 32 | 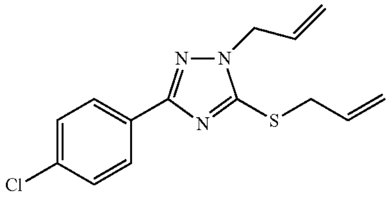 [SMILES: C=CCSc1nc(-c2ccc(Cl)cc2)nn1CC=C] | 6f | $^1$H NMR δ 8.04 (d, 2H), 7.37 (d, 2H), 5.95 (m, 2H), 5.21 (m, 4H), 4.75 (d 2H, J = 8 Hz), 3.95 (d 2H, J = 8 Hz) | 26 | 14 |
| 33 | 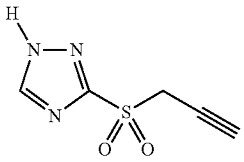 | 7a | IR: 1461, 1375 cm$^{-1}$ | 42 | 23 |

TABLE1-continued
In-vitro antimycobacterial activity of triazole derivatives against *M. bovis* BCG.
| S. N. | Chemical Structure | compound | Spectral data | Antimycobacterial activity[a] % inhibition at 100 μg/ml Aerobic/Active stage | Anearobic/Dormant stage |
|---|---|---|---|---|---|
| 34 | 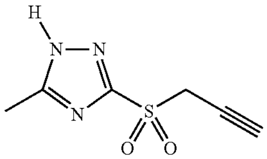 | 7b | Mass spectrum m/z 361.1515 (di), 153.0338(m-32) | 92 | 82 |
| 35 | 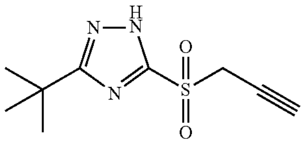 | 7c | $^1H$ NMR δ 4.03 (m, 2H), 2.60 (t, 1H), 1.22 (s, 9H) | 76 | 74 |
| 36 | 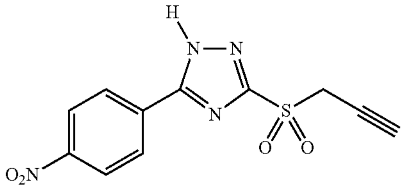 [SMILES: C#CCS(=O)(=O)c1n[nH]c(-c2ccc([N+](=O)[O-])cc2)n1] | 7d | IR: 1458 and 1377 $cm^{-1}$ | 96 | 91 |
| 37 | 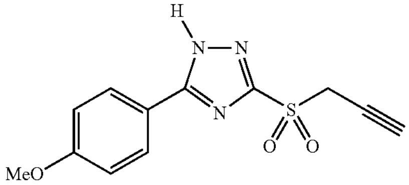 [SMILES: C#CCS(=O)(=O)c1n[nH]c(-c2ccc(OC)cc2)n1] | 7e | IR: 1461, 1375 $cm^{-1}$ | 88 | 82 |
| 38 | 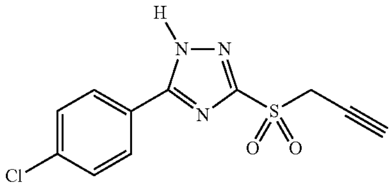 [SMILES: C#CCS(=O)(=O)c1n[nH]c(-c2ccc(Cl)cc2)n1] | 7f | | 88 | 86 |
| 39 | 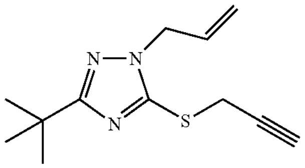 [SMILES: C#CCSc1nc(C(C)(C)C)nn1CC=C] | 8a | | 76 | 74 |
| 40 | 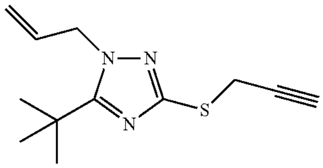 [SMILES: C#CCSc1nc(C(C)(C)C)n(CC=C)n1] | 8b | | 96 | 91 |
| 41 | 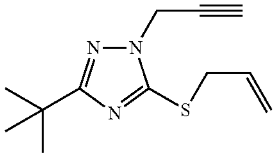 [SMILES: C#CCn1nc(C(C)(C)C)nc1SCC=C] | 8c | | 98 | 79 |

TABLE1-continued

In-vitro antimycobacterial activity of triazole derivatives against *M. bovis* BCG.

| S. N. | Chemical Structure | compound | Spectral data | Antimycobacterial activity[a] % inhibition at 100 μg/ml Aerobic/Active stage | Anearobic/Dormant stage |
|---|---|---|---|---|---|
| 42 | 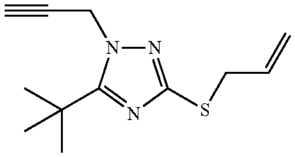 [SMILES: C#CCn1nc(SCC=C)nc1C(C)(C)C] | 8d | | 98 | 82 |
| 43 | 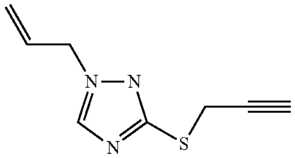 | 9b | $^1$H NMR δ 8.04 (s, 1H), 6.00 (m, 1H), 5.32 (m, 2H), 4.74 (m, 2H), 3.85 (d, 2H), 2.20 (t, 1H) | 98 | 86 |
| 44 | 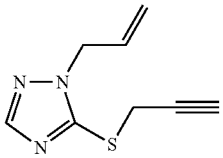 | 9a | $^1$H NMR δ 7.90 (s, 1H), 5.90 (m, 1H), 5.25 (dd, 2H), 4.74 (m, 2H), 3.93 (d, 2H), 2.24 (t, 1H) | 40 | 22 |
| 45 | 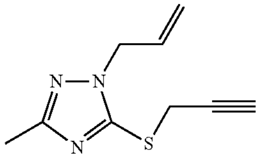 | 10a | $^1$H NMR δ 5.92 (m, 1H), 5.22 (m, 2H), 4.68 (m, 2H), 3.93 (d, 2H), 3.03 (s, 3H), 2.24 (t, 1H) | 98 | 93 |
| 46 | 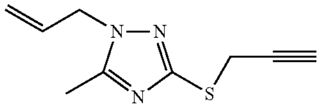 | 10b | $^1$H NMR δ 5.92 (m, 1H), 5.22 (m, 2H), 4.66 (m, 2H), 3.82 (d, 2H), 2.38 (s, 3H), 2.19 (t, 1H) | 98 | 92 |
| 47 | 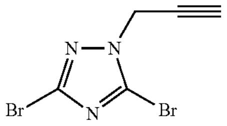 | 11a | $^1$H NMR δ 4.93 (d, 2H), 2.49 (t, 1H) | 97 | 20 |
| 48 | 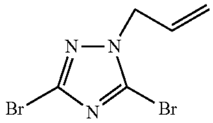 | 11b | $^1$H NMR δ 4.71(d, 2H), 5.26(M, 2H), 5.86 (m, 1H) | 12 | 21 |
| 49 | 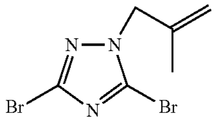 | 11c | | 09 | 19 |
| 50 | 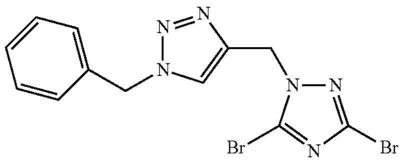 [SMILES: Brc1nc(Br)n(Cc2cn(Cc3ccccc3)nn2)n1] | 11d | $^1$H NMR δ 7.56 (s, 1H), 7.38 (m, 4H), 5.52 (s, 2H), 5.44 (s, 2H) | 2 | 13 |

Chemical name of the representative compounds are:
4-benzyl-1-[(1H-1,2,4-triazol-3-ylthio)methyl]-1H-1,2,3-triazole-methane (1:1) 1a;
4-benzyl-1-{[(5-methyl-1H-1,2,4-triazol-3-yl)thio]methyl}-1H-1,2,3-triazole-methane (1:1) 1b;
4-benzyl-1-{[(5-tert-butyl-1H-1,2,4-triazol-3-yl)thio]methyl}-1H-1,2,3-triazole-methane (1:1) 1c;
4-benzyl-1-{[(5-tert-butyl-1H-1,2,4-triazol-3-yl)thio]methyl}-1H-1,2,3-triazole-methane (1:1) 2c;
1-benzyl-4-((1-((1-benzyl-1H-1,2,3-triazol-4-yl)methyl)-5-methyl-1H-1,2,4-triazol-3-ylthio)methyl)-1H-1,2,3-triazole 2b;
1-benzyl-4-((1-((1-benzyl-1H-1,2,3-triazol-4-yl)methyl)-5-tert-butyl-1H-1,2,4-triazol-3-ylthio)methyl)-1H-1,2,3-triazole 2a;
1-benzyl-4-((1-((1-benzyl-1H-1,2,3-triazol-4-yl)methyl)-5-(4-methoxyphenyl)-1H-1,2,4-triazol-3-ylthio)methyl)-1H-1,2,3-triazole 2e;
1-benzyl-4-((1-((1-benzyl-1H-1,2,3-triazol-4-yl)methyl)-5-(4-chlorophenyl)-1H-1,2,4-triazol-3-ylthio)methyl)-1H-1,2,3-triazole 2f;
1-benzyl-4-((1-((1-benzyl-1H-1,2,3-triazol-4-yl)methyl)-1H-1,2,4-triazol-5-ylthio)methyl)-1H-1,2,3-triazole 3a;
1-benzyl-4-((1-((1-benzyl-1H-1,2,3-triazol-4-yl)methyl)-3-methyl-1H-1,2,4-triazol-5-ylthio)methyl)-1H-1,2,3-triazole 3b;
1-benzyl-4-((1-((1-benzyl-1H-1,2,3-triazol-4-yl)methyl)-3-tert-butyl-1H-1,2,4-triazol-5-ylthio)methyl)-1H-1,2,3-triazole 3c;
1-benzyl-4-((1-((1-benzyl-1H-1,2,3-triazol-4-yl)methyl)-3-(4-nitrophenyl)-1H-1,2,4-triazol-5-ylthio)methyl)-1H-1,2,3-triazole 3d;
1-benzyl-4-((1-((1-benzyl-1H-1,2,3-triazol-4-yl)methyl)-3-(4-methoxyphenyl)-1H-1,2,4-triazol-5-ylthio)methyl)-1H-1,2,3-triazole 3e;
1-benzyl-4-((1-((1-benzyl-1H-1,2,3-triazol-4-yl)methyl)-3-(4-chlorophenyl)-1H-1,2,4-triazol-5-ylthio)methyl)-1H-1,2,3-triazole 3f;
3-allylthio-1H 1,2,4 triazole 4a;
3-(allylthio)-5-methyl-1H-1,2,4-triazole 4b;
3-(allylthio)-5-tert-butyl-1H-1,2,4-triazole 4c;
3-(allylthio)-5-(4-nitrophenyl)-1H-1,2,4-triazole 4d;
3-(allylthio)-5-(4-methoxyphenyl)-1H-1,2,4-triazole 4e;
3-(allylthio)-5-(4-chlorophenyl)-1H-1,2,4-triazole 4f;
1-allyl-3-(allylthio)-1H-1,2,4-triazole 5a;
1-allyl-3-(allylthio)-5-methyl-1H-1,2,4-triazole 5b;
1-allyl-3-(allylthio)-5-tert-butyl-1H-1,2,4-triazole 5c;
1-allyl-3-(allylthio)-5-(4-nitrophenyl)-1H-1,2,4-triazole 5d;
1-allyl-3-(allylthio)-5-(4-methoxyphenyl)-1H-1,2,4-triazole 5e;
1-allyl-3-(allylthio)-5-(4-chlorophenyl)-1H-1,2,4-triazole 5f;
1-allyl-5-(allylthio)-1H-1,2,4-triazole 6a;
1-allyl-5-(allylthio)-3-methyl-1H-1,2,4-triazole 6b;
1-allyl-5-(allylthio)-3-tert-butyl-1H-1,2,4-triazole 6c;
1-allyl-5-(allylthio)-3-(4-nitrophenyl)-1H-1,2,4-triazole 6d;
1-allyl-5-(allylthio)-3-(4-methoxyphenyl)-1H-1,2,4-triazole 6e;
1-allyl-5-(allylthio)-3-(4-chlorophenyl)-1H-1,2,4-triazole 6f;
5-(prop-2-ynylsulfonyl)-1H-1,2,4-triazole 7a;
3-methyl-5-(prop-2-ynylsulfonyl)-1H-1,2,4-triazole 7b;
3-tert-butyl-5-(prop-2-ynylsulfonyl)-1H-1,2,4-triazole 7c;
3-(4-nitrophenyl)-5-(prop-2-ynylsulfonyl)-1H-1,2,4-triazole 7d;
3-(4-methoxyphenyl)-5-(prop-2-ynylsulfonyl)-1H-1,2,4-triazole 7e;
3-(4-chlorophenyl)-5-(prop-2-ynylsulfonyl)-1H-1,2,4-triazole 7f;
1-allyl-3-tert-butyl-5-(prop-2-ynylthio)-1H-1,2,4-triazole 8a;
1-allyl-5-tert-butyl-3-(prop-2-ynylthio)-1H-1,2,4-triazole 8b;
5-(allylthio)-3-tert-butyl-1-(prop-2-ynyl)-1H-1,2,4-triazole 8c;
3-(allylthio)-5-tert-butyl-1-(prop-2-ynyl)-1H-1,2,4-triazole 8d;
1-allyl-3-(prop-2-ynlthio)-1H-1,2,4-triazole 9a;
1-allyl-5-(prop-2-ynylthio)-1H-1,2,4-triazole 9b;
1-allyl-3-methyl-5-(prop-2-ynylthio)-1H-1,2,4-triazole 10a;
1-allyl-5-methyl-3-(prop-2ynylthio)-1H-1,2,4-triazole 10b;
3,5-dibromo-1-(prop-2-ynyl)-1H-1,2,4-triazole 11a;
1-allyl-3,5-dibromo-1H-1,2,4-triazole 11b;
3,5-dibromo-1-(2-methylallyl)-1H-1,2,4-triazole 11c;
1-benzyl-4-((3,5-dibromo-1H-1,2,4-triazol-1-yl)methyl)-1H-1,2,3-triazole 11d.

The triazole derivatives of the present invention can advantageously be used to treat the pathological conditions or the diseases caused by *Mycobacterium bovis* BCG and *Mycobacterium tuberculosis* H37Ra. The nitrate reductase activity was used to represent the dormant stage whereas absorbance of the culture at 620 nm was used to represent the active stage of the bacilli in this screening protocol. Compound of Formula 4f [5-(4-chlorophenyl)-{3-(prop-3-en-yl thiol)}-S-2H-1,2,4 triazole] is effective against both active as well as dormant stage of the bacilli of *M. bovis* BCG and *M. tuberculosis.*

Invention relates to a pharmaceutical composition comprising of the active ingredient of Formula I and II or their pharmaceutically acceptable salts, as defined above either alone or as its salts along with pharmaceutically acceptable excipients. The pharmaceutical composition according to the invention can be in the form of a solid, for example, powders, granules, tablets, capsules or can be present in the liquid form such as solutions, emulsions, suspensions etc or as an injectable composition. The invention also provides methods for the treatment of the disorder discussed above. The triazole derivatives of the formula I and II and pharmaceutical compositions containing them may, according to the invention, be administered using any amount, any form of pharmaceutical composition and any route of administration effective for the treatment. After formulation with an appropriate pharmaceutically acceptable carrier in a desired dosage, as known by those of skill in the art, the pharmaceutical compositions of this invention can be administered by any means that delivers the active pharmaceutical ingredient (s) to the site of the body whereby it can exert a therapeutic effect on the patient.

EXAMPLES

Following examples are given by way of illustration therefore should not construed to limit the scope of the invention.

Chemistry

All the solvents used were purified according to literature procedures. Thin layer chromatography was performed on E. merk pre coated 60F 254 plate and the spot were rendered visible by using iodine and UV light as detector. IR spectra were recorded (in chloroform as solution and nujol as mull) on a Shimadzu FTIR-8400 spectrometer. NMR spectra were recorded on Brucker AC 200 spectrometer. Chemical shift reported are referred to internal tetramethylsilane as standard. All melting points are uncorrected and were determined using a Buchi B-540 melting point apparatus. Mass spectra were recorded on Applied Biosystems, API-Q* Pulsar. X-ray were recorded on Smart-Apex X-ray defractometer.

Chemicals, Media and Strains

Unless otherwise mentioned, all the chemicals were purchased from Sigma, USA. Dubos broth base, Dubos albumin supplements were purchased from Difco, USA. Minimal essential medium, Fetal bovine serum and Fetal calf serum were purchase from GIBCO, USA. Sulphanilic acid and napthyl ethylene diaminedihydrochloride (NEDD) were purchased from Merck, India. *M. bovis* BCG (ATCC 35745) and *M. smegmatis* (ATCC 607) were obtained from AstraZeneca, India and *M. tuberculosis* H37Ra (ATCC 25177) was obtained from MTCC, India. *E. coli* DH5α was obtained from the NCIM, India. THP-1 cell line was obtained from National cell repository, NCCS India. Sub culturing of mycobacterial strains was routinely done in Dubos albumin agar slants or plates. Liquid inoculums were prepared in Dubos tween albumin broth medium, incubated in a shaker incubator rotating at a speed of 150 rpm at 37° C.

Example 1

Preparation of Triazole 1c 3-(t-butyl)-5-(prop-2-ynylthio)1H-1,2,4-triazole (700 mg) was taken in t-butanol (7 ml) and water (3 ml) mixture. To this solution benzyl azide (572 mg) was added followed by the addition of $CuSO_4$ (24 mg) and sodium ascorbate (40 mg). This reaction mixture was stirred at room temperature for 5 hr. Reaction completion was checked by TLC. t-Butanol was removed and remaining mixture extracted with ethyl acetate. Ethyl acetate layer was washed with water and brine, finally dried over $NaSO_4$ and concentrated to get solid product. This product was purified by column chromatography to get 1c (1.1 gm).

Example 2

Preparation of Ditriazoles 2c 5-(t-butyl)-1-(prop-2-ynyl)-3-(prop-2-ynylthio)1H-1,2,4-triazole (237 mg) was taken in t-butanol (7 ml) and water (3 ml) mixture. To this solution benzyl azide (310 mg) was added followed by the addition of $CuSO_4$ (48 mg) and sodium ascorbate (80 mg). This reaction mixture was stirred at room temperature for 5 hr. Reaction completion was checked by TLC. t-Butanol was removed and remaining mixture was extracted with ethyl acetate. Ethyl acetate layer was washed with water and brine, finally dried over $Na_2SO_4$ and concentrated to get solid product. This product was purified by column chromatography to get 2c (450 mg).

Example 3

Preparation of Ditriazoles 3c 3-(t-butyl)-1-(prop-2-ynyl)-5-(prop-2-ynylthio)1H-1,2,4-triazole (237 mg) was taken in t-butanol (7 ml) and water (3 ml) mixture. To this solution benzyl azide (310 mg) was added followed by the addition of $CuSO_4$ (48 mg) and sodium ascorbate (80 mg). This reaction mixture was stirred at room temperature for 5 hr. Reaction completion was checked by TLC. t-Butanol was removed and remaining mixture was extracted with ethyl acetate. Ethyl acetate layer was washed with water and brine, finally dried over $Na_2SO_4$ and concentrated to get solid product. This product was purified by column chromatography to get 3c (420 mg).

Example 4

Preparation of Allyl Derivatives 4e, 5e and 6e 3-p-methoxyphenyl-1,2,4-triazole-5-thiol (1 gm) and $K_2CO_3$ (1.46 gm) was taken in DMF (10 ml). To this solution, allyl bromide (1.28 gm) was added dropwise. Then reaction mixture was stirred further for 4 hrs. Completion of the reaction was checked by TLC. DMF was removed and residue was extracted with ethyl acetate, organic layer was washed successively with water and brine, further dried over anhydrous $Na_2SO_4$ and concentrated to get product, which was the mixture of 3 compounds as seen by TLC, which was further separated by column chromatography to get 6e (0.700 gm), 5e (0.23 gm) and 4e (0.085 gm).

Example 5

Preparation of Sulfone 7e 3-(4-methoxyphenyl)-5-prop-2-ynylthio)1H-1,2,4-triazole, (300 mg) was dissolved in 50% aq. acetone and cooled to 0° C. To this solution Oxone (1.01 gm) was added and reaction mixture was stirred at room temperature for 2 hrs. The reaction mixture was neutralized by adding aq. $NaHCO_3$ to pH-7, quenched by adding sodium metabisulphite. Reaction mixture was extracted with ethyl acetate, organic layer was washed successively with water and brine, further dried over anhydrous $Na_2SO_4$ and concentrated to get sulfone 7e (250 mg)

Example 6

Primary Screening Results

Above synthesized 50 triazole derivatives were first screened against *M. bovis* BCG using a newly developed whole cell based assay. This assay could identify the inhibitors of active as well as dormant stage inhibitor molecules. In primary screening 100 ug/ml of compound concentration was applied in order to select the hit molecules showing biological activity against *M. bovis* BCG. Out of 50 different triazole derivatives, only 25 showed more than 60% inhibition on growth of active bacilli (Table 1). These hits were further taken up for secondary screening in order to confirm their activity and select the molecules showing the maximum inhibition at lowest concentration. Subsequently, dose response effect was monitored for all these 25 actives applying a concentration range between 100 and 1 μg/ml against same aerobically growing *M. bovis* BCG.

Example 7

Biological Screening of Compounds for Antimycobacterial Activity

A protocol which can identify inhibitors of active as well as dormant tubercle bacilli, was used to screen the compounds. Nitrate reductase activity was used to represent the dormant stage whereas absorbance of the culture at 620 nm was used to represent the active stage of the bacilli in this screening protocol. 2.5 μl microliters of compound solution in DMSO was aseptically transferred to individual wells of sterile 96-well plates. 247.5 μl of *M. bovis* BCG culture containing approximately $10^5$ cells/ml, supplemented with 40 mM Na $NO_3$ was aseptically transferred to each well to make up the total volume to 250 μl and the plate was covered with a sealer. 125 μl space was left in each well to make the headspace to culture volume ratio exactly 0.5. After sealing, these culture plates were incubated at 37° C. in an incubator. After 8 days of incubation, culture OD was read at 620 nm. Then, 80 μl of culture was taken out from each well and transferred to a separate 96 well plate by using a multichannel pipette. 80 μl of 1% sulphanilic acid solution and 80 μl of 0.1% NEDD solution were added in each well of the plate and incubated for 15 minutes at room temperature to develop pink color. The color was read in Spectramax 384plus (Molecular Devices Inc. USA) at 540 nm to measure NR activity. Inhibition of aerobic and dormant phase in presence of the compounds was calculated by using equation 1 and 2.

$$\%\text{ Inhibition of active phase} = \frac{A_{620}\text{ of culture in presence of compound} - \text{blank}}{A_{620}\text{ of negative control} - \text{blank}} \times 100 \quad (1)$$

$$\%\text{ Inhibition of dormant phase} = \frac{NR\text{ activity in presence of compound} - \text{blank}}{NR\text{ activity of negative control} - \text{blank}} \times 100 \quad (2)$$

Example 8

Antimycobacterial Activity Against Dormant Bacilli

Active stage inhibitor can also be a dormant stage inhibitor, could not be identified from the above used assay. This could be identified by adding the active stage inhibitor in tube culture model of dormancy The compound was added by syringe to a culture after 8 days of inoculation when it has already reached to dormant stage. It was then further incubated for 4 days in presence of compound and effect on viability was checked by plating the culture and determining CFU/ml.

Example 9

Determination of Antitubercular Activity Against Active Replicating Bacilli

Inhibitory activity of the compounds against growing *M. bovis* BCG and *M. tuberculosis* $H_{37}Ra$ bacilli was carried out by incubating the cells in aerobic condition in 100 ml flask containing 50 ml medium, shaking at 150 rpm and 37° C. (Thermo electron Model No. 481) for the time period of 8 days. Compounds were added at the time of inoculation and growth was measured by reading absorbance at 620 nm as well as by determining CFU/ml (colony forming unit) after 8 days of incubation at which it reaches to stationary phase. The lowest concentration of drugs, yielding a differential absorbance ($A_{620}$) of approximately zero or less was defined as MIC. In order to determine the Minimum Bactericidal Concentration, 100 μl of the culture with appropriate serial dilution was identified spread on Dubos agar (1.5%) plate for monitoring colony counts after 21 days of incubation at 37° C. within 90% humidified incubator to find the effect of the inhibitors. The result was expressed as reduction in log value with respect to the vehicle control. Refer table 1.

Example 10

Determination of Antituberculous Activity Against Hypoxia Induced Dormant Bacilli Inhibitory activity of the compounds against dormant bacilli was examined by using Wayne's 0.5 HSR (head space ratio) model. The Wayne's hypoxic model is based on gradual depletion of oxygen from mycobacterial cells to achieve the non-replicating dormant stage. Briefly, 17.5 ml diluted culture of *M. bovis* BCG containing about $10^5$ cells per ml was transferred to 20×125 mm tubes. Culture tubes were then sealed with rubber septa and gently stirred with the help of 8 mm magnetic beads rotating at 100 rpm on a magnetic stirring platform at 37° C. for a time period for 8 days. Attainment of cells hypoxic non replicating dormant stage was confirmed by constant CFU/ml as well as by decolorization of methylene blue (1.5 μg/ml) dye in Wayne culture system. Once all the cells reached to non-replicating phase, 170 μl of compound solutions with 100×MIC level of aerobic culture were added by using a Hamilton syringe with a 24-gauge needle and incubated for another 4 days. 100 μl of culture samples with serial dilution were then spread on Dubos agar plates and colonies were enumerated on day 21 to examine the effect of compound on dormant stage. The result was expressed as reduction in log value with respect to the vehicle control. Refer table 1.

Advantages of the Invention

- The invention provides novel compounds which are shown to anti tubercular in activity.
- The novel compounds provided can be evaluated for other activities
- The compounds of the invention are useful in active as well as dormant phase of mycobacterium.
- The compounds can be used to formulate various pharmaceutical dosage forms.

We claim:

1. Compounds of General Formula I,

General Formula I

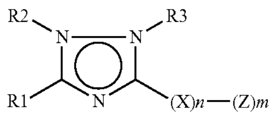

wherein,

X is sulfur (S) or a sulphone

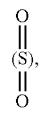

'n' is 1,

'm' is 1;

R1 is an aryl group optionally substituted with —$OCH_3$, halogen, or nitro;

R2 and R3 are selected from the group consisting of hydrogen, and $C_1$-$C_6$ alkyl optionally substituted with heterocyclic ring of 5 to 6 ring atoms containing one to three hetero atoms selected from oxygen, sulfur, nitrogen, which may be substituted with alkyl, arylalkyl, linear or branched alkenyl, substituted alkenyl, alkynyl, substituted alkynyl, or allyl or propargyl groups consisting of 1 to 6carbon atoms; and Z is $C_1$-$C_6$ alkyl optionally substituted with heterocyclic ring of 5 ring atoms, containing one to three hetero atoms selected from oxygen, sulfur, nitrogen, which may be substituted with arylalkyl, linear or branched alkenyl, substituted alkenyl, alkynyl, substituted alkynyl, allyl or propargyl groups consisting of 1 to 6 carbon atoms.

2. The compounds as claimed in claim 1, selected from the group consisting of:

1-benzyl-4-((1-((1-benzyl-1H-1,2,3-triazol-4-yl)methyl)-5-(4-methoxyphenyl)-1H-1,2,4-triazol-3-ylthio)methyl)-1H-1,2,3-triazole;

1-benzyl-4-((1-((1-benzyl-1H-1,2,3-triazol-4yl)methyl)-5-(4-chlorophenyl)-1H-1,2,4-triazol-3-ylithio)methyl)-1H-1,2,3-triazole;

1-benzyl-4-((1-((1-benzyl-1H-1,2,3-triazol-4-yl)methyl)-3-(4-methoxphenyl)-1H-1,2,4-triazol -5-ylthio)methyl)-1H-1,2,3-triazole;

1-benzyl-4-((1-((1-benzyl-1H-1,2,3-triazol-4-yl)methyl)-3-(4-methoxyphenyl)-1H-1,2,4-triazol-5-ylthio)methyl)-1H-1,2,3-triazole; and 1-benzyl-4-((1-((1-benzyl-1H-1,2,3-triazol-4-yl)methyl)-3-(4-chlorophenyl)-1H-1,2,4-triazol-5-ylthio)methyl)-1H-1,2,3-triazole.

3. The compounds as claimed in claim 1, wherein said compounds are antitubercular and are active against actively growing as well as dormant bacilli of *Mycobacterium bovis* BCG and *Mycobacterium tuberculosis* H37Ra.

* * * * *